(12) United States Patent
Pilgrim et al.

(10) Patent No.: US 11,774,461 B2
(45) Date of Patent: Oct. 3, 2023

(54) IRON CHELATOR-CONTAINING PROTHROMBIN TIME REAGENT

(71) Applicant: Siemens Healthcare Diagnostics Products GmbH, Marburg (DE)

(72) Inventors: Sabine Pilgrim, Marburg (DE); Thomas Wissel, Lahntal (DE); Norbert Zander, Marburg (DE)

(73) Assignee: Siemens Healthcare Diagnostics Products GMBH, Marburg (DE)

( * ) Notice: Subject to any disclaimer, the term of this patent is extended or adjusted under 35 U.S.C. 154(b) by 0 days.

(21) Appl. No.: 16/767,623

(22) PCT Filed: Nov. 27, 2018

(86) PCT No.: PCT/EP2018/082632
§ 371 (c)(1),
(2) Date: May 28, 2020

(87) PCT Pub. No.: WO2019/105907
PCT Pub. Date: Jun. 6, 2019

(65) Prior Publication Data
US 2020/0371119 A1    Nov. 26, 2020

(30) Foreign Application Priority Data

Nov. 28, 2017 (EP) .................................. 17204000

(51) Int. Cl.
*G01N 33/86* (2006.01)

(52) U.S. Cl.
CPC ..... *G01N 33/86* (2013.01); *G01N 2333/7454* (2013.01); *G01N 2800/224* (2013.01)

(58) Field of Classification Search
None
See application file for complete search history.

(56) References Cited

U.S. PATENT DOCUMENTS

| | | | |
|---|---|---|---|
| 3,522,148 A | 7/1970 | Adam, Jr. et al. | |
| 5,192,689 A | 3/1993 | Hemker et al. | |
| 5,677,466 A | 10/1997 | Weisenberger et al. | |
| 6,426,192 B1 | 7/2002 | Stocker et al. | |
| 6,596,750 B2 | 7/2003 | Lattmann et al. | |
| 2005/0136499 A1 | 6/2005 | Henckel | |
| 2008/0260858 A1 | 10/2008 | Morrissey et al. | |
| 2009/0061468 A1 | 3/2009 | Hoshiko et al. | |
| 2017/0016923 A1 | 1/2017 | Neilsen | |
| 2017/0234895 A1 | 8/2017 | Cawthern et al. | |

FOREIGN PATENT DOCUMENTS

| | | |
|---|---|---|
| CA | 2073741 A | 1/1993 |
| CA | 2263197 A1 | 9/1999 |
| CN | 102753189 A | 10/2012 |
| CN | 105368915 A | 3/2016 |
| CN | 107184570 A | 9/2017 |
| CN | 107356768 A | 11/2017 |
| EP | 0420332 A2 | 4/1991 |
| EP | 0524803 A2 | 1/1993 |
| EP | 0585987 A1 | 3/1994 |
| EP | 0942284 A2 | 9/1999 |
| EP | 0314118 B1 | 10/2002 |
| JP | 63275953 A | 11/1988 |
| JP | 63275954 | 11/1988 |
| JP | S63275954 A | 11/1988 |
| JP | H05207897 A | 8/1993 |
| JP | H0650977 A | 2/1994 |
| JP | H071272 A | 1/1995 |
| JP | H08168479 A | 7/1996 |
| JP | H11316228 A | 11/1999 |
| JP | 2002506515 A1 | 2/2002 |
| JP | 2002156379 A | 5/2002 |
| JP | 2009058393 A | 3/2009 |
| JP | 2014232003 A | 12/2014 |
| WO | WO 9849562 A1 | 11/1998 |
| WO | WO 2017139567 A1 | 8/2017 |

OTHER PUBLICATIONS

Parkins, D.A., et al. 2000 PSTT 3(4): 129-137. (Year: 2000).*
Lobo, V., et al. 2010 Pharmacognosy Reviews 4(8): 118-126. (Year: 2010).*
Ortega-Guitérrez, S., et al. 2002 Neuroscience Letters 323: 55-59. (Year: 2002).*
Basaran, U.N., et al. 2013 The Scientific World Journal Article ID 376959: 7 pages. (Year: 2013).*
Zu D. Liu et al: "Design of clinically useful iron(III)-selective chelators", Medicinal Research Reviews, vol. 22, No. 1, Jan. 2001 (Jan. 1, 2001), pp. 26-64, XP055210372; ISSN: 0198-6325, DOI: 10.1002/med.1027; 2001.
Rossi et al: "In vitro chelating cytotoxicity, and blood compatibility of degradable poly(ethylene glycol)-based macromolecular iron chelators"; Biomaterials; No. 30 (2009); pp. 638-648; XP025693622; ISSN: 0142-9612.
Lawrie, A.S. et al., Prothrombin time derived fibrinogen determination on Sysmex CA-6000TM, J. Clin.Pathol, 1998, 51:462-466.
Hemker, H.C. et al., The Thrombogram: Monitoring Thrombin Generation in Platelet Rich Plasma, Thromb Haemost 2000; 83: 589-591.
Guideline, Guidelines on Fibrinogen Assays, British Journal of Haematology, 2003, 121, 393-404.
Zhang, Jinlian et al., Preparation of liquid thromboplastin reagent and its quality evaluation, Journal of Xinxiang Medical University, vol. 19, No. 2, Apr. 30, 2002.

(Continued)

Primary Examiner — Marsha Tsay

(74) Attorney, Agent, or Firm — BakerHostetler

(57) ABSTRACT

The present invention pertains to the field of coagulation diagnostics and relates to a prothrombin time reagent on the basis of recombinant or native tissue factor protein and phospholipids, which reagent can be stabilized by the addition of an iron chelator from the groups of siderophores and 3,5-diphenyl-1,2,4-triazoles.

16 Claims, 2 Drawing Sheets

(56) References Cited

OTHER PUBLICATIONS

Buettner et al., Catalytic Metals, Ascorbate and Free Radicals: Combinations to Avoid, Radiation Research, 145, pp. 532-541 (1996).

Graf et al., Iron-catalyzed Hydroxyl Radical Formation, The Journal of Biological Chemistry, vol. 259, No. 6, Mar. 25, 1984, pp. 3620-3624.

* cited by examiner

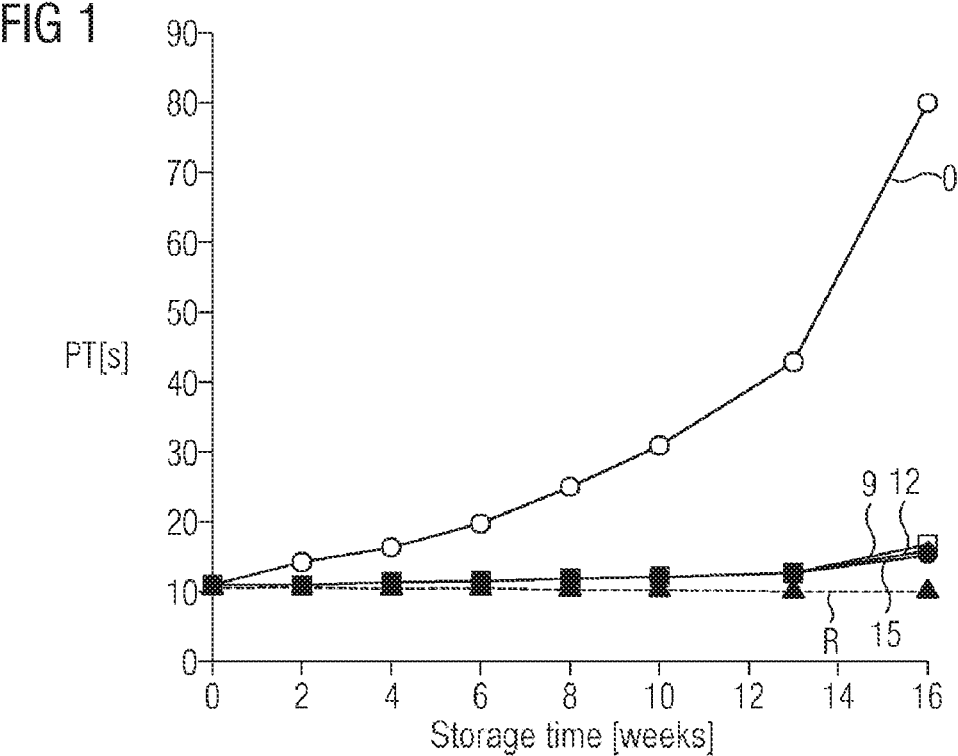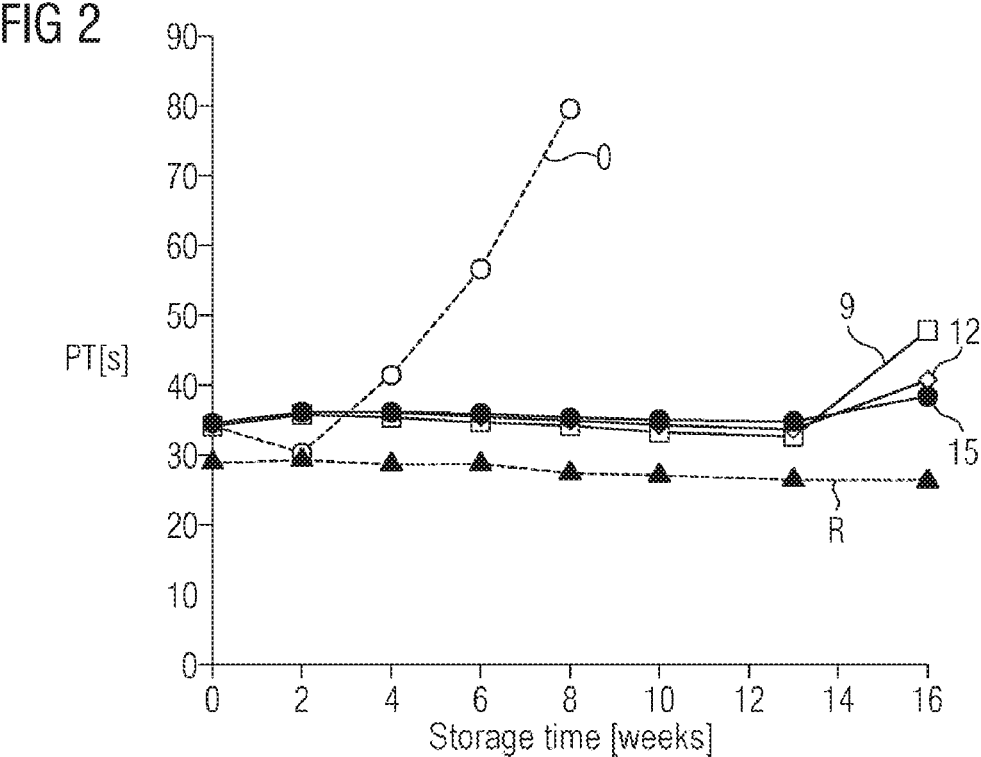

IRON CHELATOR-CONTAINING PROTHROMBIN TIME REAGENT

CROSS-REFERENCE TO RELATED APPLICATIONS

This application is a 35 U.S.C. § 371 national phase application of International Patent Application No. PCT/EP2018/082632, filed Nov. 27, 2018, which claims priority to European application No. 17204000.8, filed Nov. 28, 2017, the entire disclosures of each of which are incorporated herein by reference in their entirety.

DESCRIPTION

The present invention is in the field of coagulation diagnosis and relates to a prothrombin time reagent based on recombinant or native tissue factor protein and phospholipids, which can be stabilized by the addition of an iron chelator selected from the group comprising a siderophore and 3,5-diphenyl-1,2,4-triazole.

Tissue factor protein (abbreviated as tissue factor or thromboplastin) is a transmembrane protein of essential importance for blood coagulation. It is expressed by cells that ordinarily are not in contact with the bloodstream, such as e.g. cells in the subendothelium (smooth muscles) and cells surrounding blood vessels (e.g. fibroblasts). In the case of damage to a blood vessel, however, the tissue-factor-protein-expressing cells come into contact with factor VII, a procoagulant blood coagulation factor that circulates in the blood. In the presence of calcium, tissue factor protein and factor VII form a complex, and the activity of factor VII is multiplied a thousand fold (F VII>F VIIa). In the presence of phospholipids and calcium, the complex of tissue factor protein and factor VIIa catalyses conversion of the inactive blood coagulation factor factor X into activated factor Xa and thus accelerates the coagulation process. Together with factor VII, the tissue factor forms the so-called extrinsic pathway of blood coagulation, via which damage to the blood vessels is to be prevented by blood clotting as rapidly as possible.

In coagulation diagnosis, various in vitro test methods have been developed by means of which one can determine whether the blood or plasma of a patient can clot without problems or whether a clotting disorder is present. In the case of a clotting disorder, it is often necessary to obtain more precise information on the cause of the disorder present in order to allow the optimum therapeutic measures to be selected. Tissue factor protein is used as an activator for investigating various partial functions of blood coagulation, in particular for investigating the extrinsic blood coagulation system. The most widely known application of tissue factor protein as a coagulation activator is the so-called Quick test for determining prothrombin time (PT) (synonym: thromboplastin time). In the Quick test and its variants, a plasma sample is ordinarily mixed with a mixture of tissue factor protein, phospholipids and calcium ions, and the duration in seconds from the time of mixing until detectable fibrin formation is measured. Alternatively, in clotting tests in which chromogenic substrates are used, one measures the duration from the time of mixing until a specified change in absorption is achieved. Tissue factor protein is also used in other test methods that serve not to determine a clotting time but to determine individual components of the coagulation system, such as e.g. endogenous thrombin potential (ETP) (EP-A2-420332). In principle, tissue factor protein can be used in all tests involving the components of intrinsic coagulation.

Prothrombin time reagent (tissue factor reagent, PT reagent) is of central importance in the respective test. Ordinarily, a prothrombin time reagent comprises the tissue factor together with coagulant-active phospholipids. The tissue factor protein is either obtained as a tissue extract from various organs (e.g. the brain, placenta, lungs) of various species (e.g. rabbits, humans, cattle) or produced by recombination. Numerous methods for obtaining tissue factor protein and producing prothrombin time reagents are known from the prior art, and numerous prothrombin time reagents are commercially available.

At present, most commercial prothrombin time reagents are sold in freeze-dried form and must therefore be dissolved prior to use in a reconstitution medium, e.g. in distilled water or a buffer solution. The reason for this is the poor stability of the reagents in a liquid state. The drawback of reagents provided in freeze-dried form is not only that the manufacturer and user must carry out additional time- and cost-intensive method steps (lyophilization and reconstitution), but also that these additional steps give rise to the risk of errors that can impair the quality of the reagent. Liquid, ready-to-use reagent formulations are therefore desirable. However, a problem in providing liquid prothrombin time reagents is their poor stability. The stability of a prothrombin time reagent can for example be understood to be maintenance of the prothrombin time for a specified plasma, e.g. a normal plasma, over the storage period. Ideally, a prothrombin time reagent should maintain its specifications throughout the duration of its storage or use, or in the most favourable case should maintain the properties and characteristics it had at the time of its production.

Various strategies for stabilizing liquid prothrombin time reagents have been described in the prior art. EP-A2-942284 describes a liquid prothrombin time reagent based on recombinant tissue factor that is stabilized by the combined addition of ascorbic acid and a serum albumin. U.S. Pat. No. 3,522,148 describes a (natural) liquid prothrombin time reagent extracted from tissue that is stabilized by the addition of specified sodium or calcium salts. EP-A1-585987 describes another liquid prothrombin time reagent based on natural tissue factor protein that is stabilized by the addition of various stabilizers, such as albumin or polyethylene glycol, and various antimicrobially active substances, such as sodium azide or antibiotics. EP-A2-524803 describes a method for preparing a prothrombin time reagent in which a metal ion chelator, in particular EDTA or EGTA, is used in extraction of the tissue factor and can be contained in the finished reagent. The amount of calcium ions bound by the metal ion chelator is replaced by adding additional calcium salt.

US 2017/0234895 A1 describes a two component kit for preparing a ready-to-use liquid prothrombin time reagent that comprises in a first container a first solution comprising tissue factor protein and phospholipids and in a second container a calcium chloride solution. The first solution comprises a calcium chelator for stabilizing purposes. The two solutions are first mixed with each other by the user shortly before use. Although the manufacturer can dispense with lyophilization and the user can dispense with reconstitution of a lyophilized reagent, the user must still mix the two liquids with each other in order to obtain the ready-to-use prothrombin time reagent.

The object of the present invention is therefore to provide a prothrombin time reagent that shows long-term stability in a liquid state and is ready to use, which can comprise at least tissue factor protein and phospholipids and can optionally also comprise calcium ions.

It was found that the addition of an iron chelator, in particular an iron chelator from the group comprising the siderophores and among them in particular the addition of deferoxamine, pyoverdine or ferrichrome or the addition of an iron chelator from the group comprising the 3,5-diphenyl-1,2,4-triazoles and among them in particular the addition of deferasirox, increases the stability of an aqueous solution comprising the tissue factor and phospholipids and optionally calcium ions. Prothrombin time reagents stabilized and stored in a liquid state according to the invention still yield after 10-week storage at +37° C. prothrombin time (PT) measurement results that deviate less than from the PT measurement result at the beginning of the run time. Forced storage at +37° C. for 10 weeks is carried out in order to rapidly evaluate whether storage stability at +2° C. to +8° C. over a period of 12 or more months can be expected. If a stabilized prothrombin time reagent in storage at +37° C. over a period of 10 weeks yields prothrombin time (PT) measurement results that deviate less than 20% from the PT measuring result at the beginning of the run time, the reagent can be expected to be stable at a storage temperature of +2° C. to +8° C. over a period of 12 or more months.

The object of the present invention is therefore a prothrombin time reagent comprising tissue factor protein and phospholipids, further comprising at least one iron chelator, wherein the at least one iron chelator is selected from the group comprising a siderophore and 3,5-diphenyl-1,2,4-triazole.

Siderophores are a class of iron-binding chelating agents that are formed from microorganisms such as bacteria and fungi and from plants and show a high affinity for Iron-III ions ($Fe^{3+}$ ions). Preferred siderophores are siderophores from the group of the hexadentate hydroxamates, such as e.g. deferoxamine, ferrichrome and ferricrocin.

Preferably, the iron chelator from the group of the siderophores is selected from the group comprising deferoxamine, pyoverdine and ferrichrome.

In an embodiment, a prothrombin time reagent according to the invention comprises the iron chelator deferoxamine from the group of the hexadentate hydroxamates (synonym: deferoxamine; brand name: Desferal), which for example is formed from the bacterium *Streptomyces pilosus*.

In another embodiment, a prothrombin time reagent according to the invention comprises the iron chelator pyoverdine, a non-ribosomal peptide that is formed for example from the bacterium *Pseudomonas fluorescens* and is classified in the group of the hexadentate mixed hydroxamate- and catecholate-type siderophores. Other suitable iron chelators from the group of the hexadentate mixed hydroxamate- and catecholate-type siderophores are for example heterobactin and yersinibactin. In yet another embodiment, a prothrombin time reagent according to the invention comprises the iron chelator ferrichrome, a cyclic hexapeptide composed of three glycine and hydroxylated and acetylated ornithine radicals (synonym: deferriferrichrome), which is formed for example from the fungus *Ustilago sphaerogena* and is also classified in the group of the hexadentate hydroxamates.

3,5-diphenyl-1,2,4-triazoles are a class of iron-binding chelating agents that were developed, among other applications, for therapeutic purposes (EP-B1-0914118). Preferred 3,5-diphenyl-1,2,4-triazoles are deferasirox, ethyl[3,5-bis(2-hydroxyphenyl)-[1,2,4]triazol-1-yl]acetate and 3,5-bis(2-hydroxyphenyl)-1-(2,2,2-trifluoroethyl)-1H-[1,2,4]triazole.

In a corresponding embodiment, a prothrombin time reagent according to the invention comprises an iron chelator from the group of the 3,5-diphenyl-1,2,4-triazoles, among them in particular deferasirox (IUPAC name: 4-[(3Z,5E)-3,5-bis(6-oxocyclohexa-2,4-dien-1-ylidene)-1,2,4-triazolidin-1-yl]benzoic acid), ethyl[3,5-bis(2-hydroxyphenyl)-[1,2,4]triazol-1-yl]acetate or 3,5-bis(2-hydroxyphenyl)-1-(2,2,2-trifluoroethyl)-1H-[1,2,4]triazole.

A prothrombin time reagent according to the invention comprises one of the above-mentioned suitable iron chelators, preferably in a concentration of 0.007 to 2.5 mmol/L, particularly preferably 0.01 to 0.5 mmol/L.

A prothrombin time reagent according to the invention can comprise one individual or a combination of two, three, four, or more of the above-mentioned suitable iron chelators.

In a particularly preferred embodiment, a prothrombin time reagent according to the invention further comprises calcium ions. For this purpose, the prothrombin time reagent can comprise calcium chloride, preferably in a concentration of 5 to 500 mmol/L.

The tissue factor protein contained in the prothrombin time reagent is preferably selected from the group comprising human or animal (e.g. rabbit, bovine, etc.) recombinant tissue factor protein and natural human or animal tissue factor protein from a tissue extract (e.g. from the brain, placenta, lung, etc.).

The phospholipids can be derived from natural and/or synthetic sources.

Although the particular advantage of the present invention lies in that a prothrombin time reagent according to the invention can be stored as a ready-to-use liquid reagent, it is of course also possible for the reagent to be provided as a lyophilizate that is reconstitutable in water or buffer.

A further object of the present invention is a method for preparing a liquid prothrombin time reagent, wherein a liquid comprising tissue factor protein, phospholipids and at least one iron chelator selected from the group comprising siderophores, among them preferably deferoxamine, pyoverdine or ferrichrome, and a 3,5-diphenyl-1,2,4-triazole, among them preferably deferasirox, ethyl[3,5-bis(2-hydroxyphenyl)-[1,2,4]triazol-1-yl]acetate or 3,5-bis(2-hydroxyphenyl)-1-(2,2,2-trifluoroethyl)-1H-[1,2,4]triazole, is provided and filled into a reagent vial without this liquid being lyophilized.

Yet a further object of the present invention is a method for stabilizing a prothrombin time reagent comprising tissue factor protein and phospholipids and optionally $Ca^{2+}$ ions, in which at least one iron chelator selected from the group comprising siderophores, among them preferably deferoxamine, pyoverdine or ferrichrome, and 3,5-diphenyl-1,2,4-triazole, preferably deferasirox, ethyl[3,5-bis(2-hydroxyphenyl)-[1,2,4]triazol-1-yl]acetate or 3,5-bis(2-hydroxyphenyl)-1-(2,2,2-trifluoroethyl)-1H-[1,2,4]triazole is added to the reagent.

In the stabilization method according to the invention, the iron chelator is preferably added in an amount such that the reagent finally comprises the iron chelator in a concentration of 0.007 to 2.5 mmol/L, particularly preferably 0.01 to 0.5 mmol/L.

Another object of the present invention is the use of a prothrombin time reagent according to the invention in an in vitro method for determining a coagulation parameter in a patient sample, in particular for determining a coagulation parameter from the group of prothrombin time (PT, also Quick test) and variants thereof, prothrombin time derived fibrinogen and endogenous thrombin potential (ETP). The reagent according to the invention is suitable for use as an activator of the coagulation cascade, for example in test methods based on the detection of a fibrin clot and also in chromogenic or fluorogenic test methods.

The invention further relates to a method for determining a coagulation parameter in a plasma sample, wherein the plasma sample is mixed with a prothrombin time reagent according to the invention to give a reaction mixture and the coagulation parameter is determined in the reaction mixture. The coagulation parameter can for example be the prothrombin time or the endogenous thrombin potential of a sample, for example a human whole blood or plasma sample.

In order to determine the prothrombin time, the change in absorption of the reaction mixture is preferably photometrically measured, and the duration from the time of mixing of the prothrombin time reagent according to the present invention with the plasma sample until reaching a threshold value is determined.

In order to derive the fibrinogen concentration from the prothrombin time determination ("derived fibrinogen"), the increase in absorption of the reaction mixture is photometrically measured; this correlates with the fibrinogen concentration.

The invention further relates to the use of an iron chelator for preparing a prothrombin time reagent comprising tissue factor protein and phospholipids, wherein the iron chelator is selected from the group comprising a siderophore and a 3,5-diphenyl-1,2,4-triazole. Preferably used iron chelators from the group of the siderophores are selected from the group comprising deferoxamine, pyoverdine and ferrichrome. Preferably used iron chelators from the group of the 3,5-diphenyl-1,2,4-triazoles are selected from the group comprising deferasirox, ethyl[3,5-bis(2-hydroxyphenyl)-[1,2,4]triazol-1-yl]acetate and 3,5-bis(2-hydroxyphenyl)-1-(2,2,2-trifluoroethyl)-1H-[1,2,4]triazole.

DESCRIPTION OF THE FIGURES

FIG. 1 shows the change in prothrombin times in seconds (PT [s]) of the normal control plasma Ci-Trol 1 with the deferoxamine-stabilized PT reagents (9=9 mg/L=0.0137 mM deferoxamine; 12=12 mg/L=0.0183 mM deferoxamine; 15=15 mg/L=0.0228 mM deferoxamine) compared to the unstabilized PT reagent without deferoxamine (0=0 mg/L=0 mM deferoxamine) and the reference reagent (R) stored lyophilized and then freshly dissolved over time (t) in weeks. The reagents were stored at a temperature of 37° C.

FIG. 2 shows the change in prothrombin times in seconds (PT [s]) of the abnormal control plasma Ci-Trol 2 with the deferoxamine-stabilized PT reagents (9=9 mg/L=0.0137 mM deferoxamine; 12=12 mg/L=0.0183 mM deferoxamine; 15=15 mg/L=0.0228 mM deferoxamine) compared to the unstabilized PT reagent without deferoxamine (0=0 mg/L=0 mM deferoxamine) and the reference reagent (R) stored lyophilized and then freshly dissolved over time (t) in weeks. The reagents were stored at a temperature of 37° C.

The following exemplary embodiments serve the purpose of clarifying the present invention and are not to be understood as limitative.

Example 1: Determination of the Stability of a Liquid Deferoxamine-Stabilized Prothrombin Time Reagent At time to, deferoxamine (Deferoxamine mesylate salt, Sigma-Aldrich Chemie GmbH, Steinheim, Germany) was added in various batches to a liquid prothrombin time reagent comprising recombinant human tissue factor protein, synthetic phospholipids, and calcium ions in the final concentrations indicated:

1. 0 mM deferoxamine,
2. 0.0137 mM (9 mg/L) deferoxamine,
3. 0.0183 mM (12 mg/L) deferoxamine,
4. 0.0228 mM (15 mg/L) deferoxamine,
5. 0.114 mM (75 mg/L) deferoxamine,
6. 0.228 mM (150 mg/L) deferoxamine.

The various reagents were used in an automatic prothrombin time test (PT test) in a Sysmex® CA-1500 analyser (Sysmex Corp., Kobe, Japan). The following defined control plasmas were used as samples:

Dade® Ci-Trol® Coagulation Control Level 1 (Ci-Trol 1) control plasma; normal control for determination of prothrombin time; the results are comparable to those with fresh normal citrate plasma;

Dade® Ci-Trol® Coagulation Control Level 2 (Ci-Trol 2) control plasma; abnormal control for determination of prothrombin time as observed in clotting disorders; the clotting times are prolonged compared to those with fresh normal citrate plasma.

The samples and reagents respectively were pre-heated to 37° C. and then mixed. The addition of the reagent triggered the clotting process, and the time until formation of the fibrin clot was measured (prothrombin time in seconds).

In order to determine the long-term stability of the various reagents, the reagents were stored in a liquid state in stoppered glass vials at +37° C. over a period of 16-18 weeks. About every two weeks, samples of the reagents were taken, and the prothrombin time of the same reference plasma was determined. At each point in time, as a reference reagent, a lyophilized prothrombin time reagent (Dade® Innovino reagent, Siemens Healthcare Diagnostics Products GmbH, Germany) was freshly reconstituted with distilled water and measured.

In FIG. 1 (Ci-Trol 1 as a sample) and FIG. 2 (Ci-Trol 2 as a sample), the prothrombin times of the various prothrombin time reagents (0, 12, 15 mg/L deferoxamine) over a period of 16 weeks at +37° C. are shown. Stable prothrombin times over a period of at least 10 weeks with deviations of less than 20% relative to the initial value at time to were achieved only with the lyophilized and in each case freshly dissolved reference reagent (R) and with the deferoxamine-stabilized prothrombin time reagents according to the invention. The reagent stored in a liquid state without deferoxamine yielded only sharply deviating prothrombin times at the latest after 4 weeks.

Figure 3:
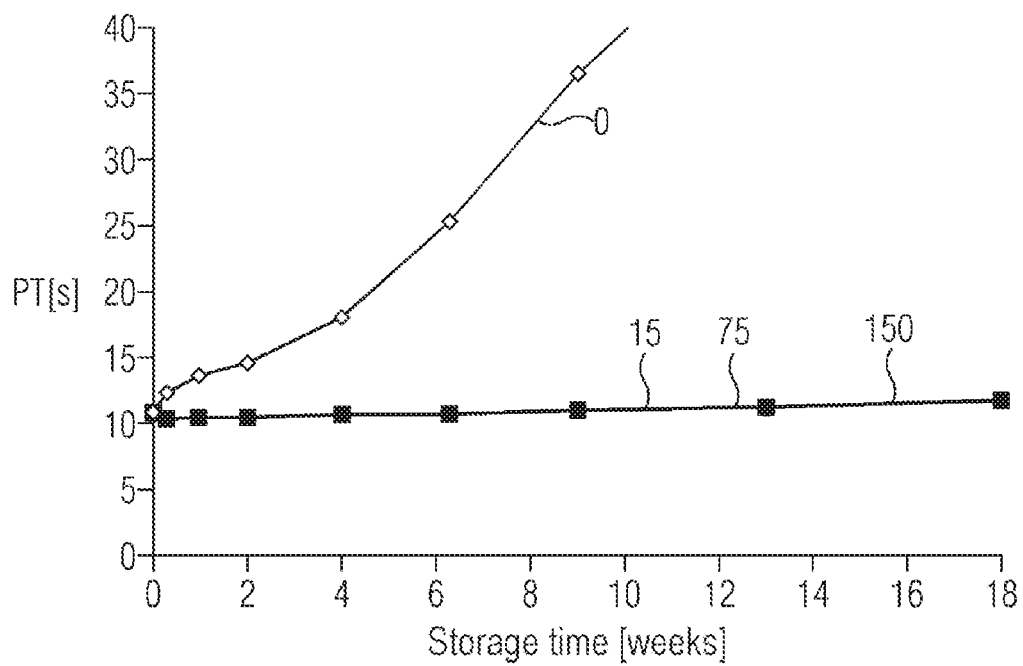
FIG. 3 shows the change in prothrombin times in seconds (PT [s]) of the normal control plasma Ci-Trol 1 with the deferoamine-stabilized PT reagents (15=15 mg/L=0.0228 mM deferoxamine; 75=75 mg/L=0.114 mM deferoxamine; 150=150 mg/L=0.228 mM deferoxamine) compared to the unstabilized PT reagent without deferoxamine (0=0 mg/L=0 mM deferoxamine) over time (t) in weeks. The reagents were stored at a temperature of 37° C.
Figure 4:
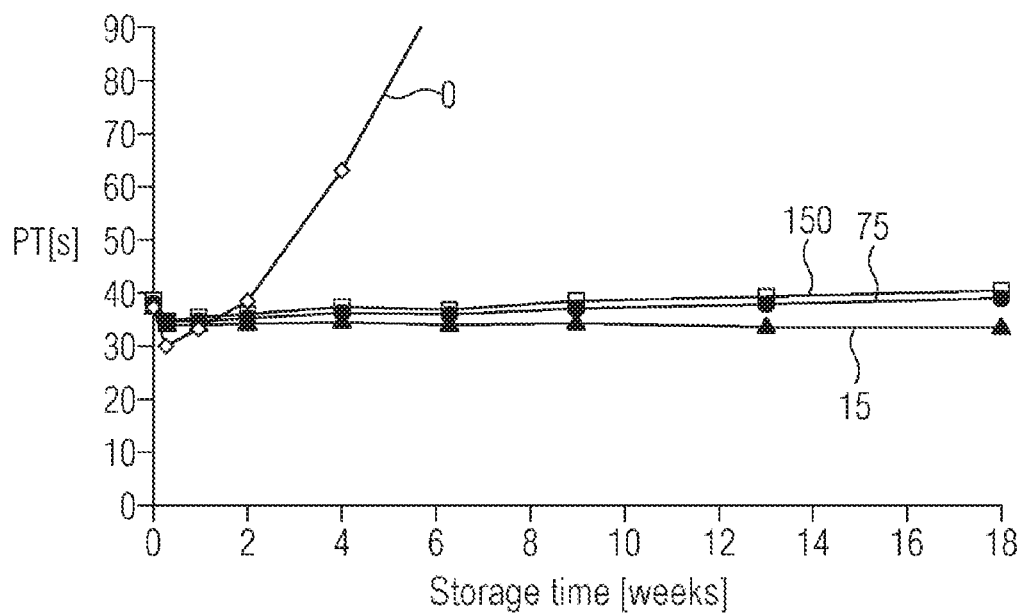
FIG. 4 shows the change in prothrombin times in seconds (PT [s]) of the abnormal control plasma Ci-Trol 2 with the deferoxamine-stabilized PT reagents (15=15 mg/L=0.0228 mM deferoxamine; 75=75 mg/L=0.114 deferoxamine; 150=150 mg/L=0.223 mM deferoxamine) compared to the unstabilized PT reagent without deferoxamine (0=0 mg/L=0 mM deferoxamine) over time (t) in weeks. The reagents were stored at a temperature of 37° C.

In FIG. 3 (Ci-Trol 1 as a sample) and FIG. 4 (Ci-Trol 2 as a sample), the prothrombin times of the various prothrombin time reagents (15, 75, 150 mg/L deferoxamine) over a period of 18 weeks at +37° C. are shown. Stable prothrombin times over a period of at least 10 weeks with deviations of less than 20% relative to the baseline at time to were achieved only with the deferoxamine-stabilized prothrombin time reagents according to the invention. The reagent stored in a liquid state without deferoxamine yielded only sharply deviating prothrombin times at the latest after 4 weeks.

Example 2: Determination of the Stability of Liquid Prothrombin Time Reagents Stabilized with Various Iron Chelators At time to, 0.0228 mmol/L each of the following metal ion chelators was added in various batches to a liquid prothrombin time reagent comprising recombinant human tissue factor protein, synthetic phospholipids, and calcium ions:

i. Pyoverdine (Pyoverdines, Sigma-Aldrich Chemie GmbH, Steinheim, Germany);
ii. Ferrichrome (Ferrichrome Iron-free from *Ustilago sphaerogena*, Sigma-Aldrich Chemie GmbH, Steinheim, Germany);
iii. Deferoxamine (Deferoxamine mesylate salt, Sigma-Aldrich Chemie GmbH, Steinheim, Germany) Deferoxamine (Deferoxamine mesylate salt, Sigma-Aldrich Chemie GmbH, Steinheim, Germany);
iv. Deferasirox (Combi-Blocks, Inc., San Diego, USA); v. DTPA (diethylenetriaminepentaacetic acid);
vi. EDTA (ethylenediaminetetraacetic acid);
vii. BAPTA (1,2-bis(2-aminophenoxy)ethane-N,N,N',N'-tetraacetic acid).

The various reagents were used as described in example 1 in an automatic prothrombin time test (PT test) in a Sysmexf CA-1500 analyser (Sysmex Corp., Kobe, Japan). The control plasmas Ci-Trol 1 and Ci-Trol 2 described in further detail in example 1 were used as samples.

In order to determine the long-term stability of the various reagents, the reagents were stored in a liquid state in stoppered glass vials at +37° C. over a period of 16-18 weeks. Samples of the reagents were taken approximately monthly, and the prothrombin time of the same reference plasma was determined.

The various measurement results (prothrombin time in seconds, PT [s]) at time to, after two- and four-month storage (2 M, 4 M) and the corresponding deviation in % from the prothrombin time measurement at time to are shown in Table 1 (Ci-Trol 1 control plasma as a sample) and in Table 2 (Ci-Trol 2 control plasma as a sample).

TABLE 1

| Chelator | $t_0$ PT [s] | 2 M PT [s] | 4 M PT [s] | 2 M % | 4 M % |
|---|---|---|---|---|---|
| Pyoverdine | 12.0 | 11.8 | 13.4 | −1.7 | 11.7 |
| Ferrichrome | 12.1 | 11.9 | 12.9 | −1.7 | 6.6 |
| Deferoxamine | 11.6 | 11.5 | 13.1 | −0.9 | 12.9 |
| Deferasirox | 11.6 | 11.4 | 13.8 | −1.7 | 19.0 |
| DTPA | 11.6 | 12.5 | 22.4 | 7.8 | 93.1 |
| EDTA | 11.8 | 35.9 | 71.5 | 204.2 | 505.9 |
| BAPTA | 11.6 | 40.2 | 72.8 | 246.6 | 527.6 |
| No chelator | 11.6 | 36.7 | 71.7 | 216.4 | 512.9 |

TABLE 2

| Chelator | $t_0$ PT [s] | 2 M PT [s] | 4 M PT [s] | 2 M % | 4 M % |
|---|---|---|---|---|---|
| Pyoverdine | 43.5 | 37.6 | 38.7 | −13.6 | −11.0 |
| Ferrichrome | 44.4 | 38.8 | 40.0 | −12.6 | −9.9 |
| Deferoxamine | 39.5 | 36.3 | 37.1 | −8.1 | −6.1 |
| Deferasirox | 38.9 | 32.8 | 43.5 | −15.7 | 11.8 |
| DTPA | 39.0 | 39.1 | 82.0 | 0.3 | 110.3 |
| EDTA | 40.2 | 100.0 | 100.0 | 148.8 | 148.8 |
| BAPTA | 39.1 | 100.0 | 100.0 | 155.8 | 155.8 |
| No chelator | 38.8 | 100.0 | 100.0 | 157.7 | 157.7 |

Stable prothrombin times over a period of four months (i.e. at least 16 weeks) with deviations of less than 20% relative to the baseline at time to were achieved only with the iron chelators according to the invention, i.e. prothrombin time reagents stabilized with pyoverdine, ferrichrome, deferoxamine or deferasirox. Both the reagent stored in liquid form without a chelator and the reagents stored in liquid form to which the metal ion chelators DTPA, EDTA or BAPTA known from the prior art (US 2017/0234895 A1) were added showed only strongly deviating prothrombin times at the latest after 4 months.

Example 3: Determination of the Stability of Liquid Prothrombin Time Reagents Stabilized with Various Iron Chelators in the Presence of Elevated $Fe^3$ Ion Concentrations At time to, 0.00308 mM (0.5 mg/L) $FeCl_3$ was added to a liquid prothrombin time reagent comprising recombinant human tissue factor protein, synthetic phospholipids, and calcium ions, and then 0.0228 mM each of the metal ion chelators mentioned in example 2 was added in various batches.

The various reagents were used as described in example 1 in an automatic prothrombin time test (PT test) in a Sysmexf CA-1500 analyser (Sysmex Corp., Kobe, Japan). The control plasmas Ci-Trol 1 and Ci-Trol 2 described in further detail in example 1 were used as samples.

In order to determine the long-term stability of the various reagents in the presence of elevated $Fe^{3+}$ ion concentrations, the reagents were stored in a liquid state in stoppered glass vials at +37° C. over a period of 6 weeks. Samples of the reagents were taken weekly, and the prothrombin time of the same reference plasma was determined.

The various measurement results (prothrombin time in seconds, PT [s]) at time to, after one-, two-, four- and six-week storage (1 W, 2 W, 4 W, 6 W) and the corresponding deviation in % from the prothrombin time measurement at time to are shown in Table 3 (Ci-Trol 1 control plasma as a sample) and in Table 4 (Ci-Trol 2 control plasma as a sample).

TABLE 3

| Chelator | $t_0$ PT [s] | 1 W PT [s] | 2 W PT [s] | 4 W PT [s] | 6 W PT [s] | 1 W % | 2 W % | 4 W % | 6 W % |
|---|---|---|---|---|---|---|---|---|---|
| Pyoverdine | 12 | 11.2 | 11.4 | 11.5 | 11.4 | −6.7 | −5 | −4.2 | −5 |
| Ferrichrome | 12.1 | 11.2 | 11.4 | 11.6 | 11.6 | −7.4 | −5.8 | −4.1 | −4.1 |
| Deferoxamine | 11.4 | 10.7 | 11 | 11.1 | 11.2 | −6.1 | −3.5 | −2.6 | −1.8 |
| Deferasirox | 11.6 | 10.9 | 10.9 | 11.1 | 11.4 | −6 | −6 | −4.3 | −1.7 |
| DTPA | 11.8 | 13 | 13.4 | 14.9 | 17.7 | 10.2 | 13.6 | 26.3 | 50 |
| EDTA | 11.6 | 13 | 15.9 | 30.2 | 49.6 | 12.1 | 37.1 | 160.3 | 327.6 |
| BAPTA | 11.6 | 13.2 | 17.7 | 38.3 | 60.8 | 13.8 | 52.6 | 230.2 | 424.1 |
| No chelator | 11.4 | 13.1 | 17.9 | 48.9 | 59.5 | 14.9 | 57 | 328.9 | 421.9 |

TABLE 4

| Chelator | $t_0$ PT [s] | 1 W PT [s] | 2 W PT [s] | 4 W PT [s] | 6 W PT [s] | 1 W % | 2 W % | 4 W % | 6 W % |
|---|---|---|---|---|---|---|---|---|---|
| Pyoverdine | 44 | 39.6 | 40 | 40.1 | 35.5 | −10 | −9.1 | −8.9 | −19.3 |
| Ferrichrome | 44.4 | 39.1 | 39.5 | 40.3 | 38.9 | −11.9 | −11 | −9.2 | −12.4 |
| Deferoxamine | 38 | 32.7 | 35.4 | 35.2 | 35.9 | −13.9 | −6.8 | −7.4 | −5.5 |
| Deferasirox | 39 | 35.1 | 33.5 | 31.2 | 32 | −10 | −14.1 | −20.0 | −17.9 |
| DTPA | 39.6 | 28.8 | 30.4 | 39.2 | 55.7 | −27.3 | −23.2 | −1 | 40.7 |
| EDTA | 38.6 | 30.6 | 50 | 100 | 100 | −20.7 | 29.5 | 159.1 | 159.1 |
| BAPTA | 38.6 | 32.7 | 61.8 | 100 | 100 | −15.3 | 60.1 | 159.1 | 159.1 |
| No chelator | 38.4 | 32.1 | 64.8 | 100 | 100 | −16.4 | 68.8 | 160.4 | 160.4 |

Stable prothrombin times over a period of six weeks with deviations of less than 20% relative to the baseline at time to were achieved in the presence of elevated $Fe^{3+}$ ion concentrations only with the iron chelators according to the invention, i.e. with the prothrombin time reagents stabilized with pyoverdine, ferrichrome, deferoxamine or deferasirox. Both the reagent stored in liquid form without a chelator and the reagents stored in liquid form to which the metal ion chelators DTPA, EDTA or BAPTA known from the prior art (US 2017/0234895 A1) were added showed only strongly deviating prothrombin times at the latest after 2 weeks.

The invention claimed is:

1. A prothrombin time reagent comprising tissue factor protein and phospholipids, wherein the reagent further comprises at least one iron chelator, wherein the at least one iron chelator is a 3,5-diphenyl-1,2,4-triazole selected from the group consisting of deferasirox, ethyl [3,5-bis(2-hydroxyphenyl)-[1,2,4]triazol-1-yl]acetate, and 3,5-bis(2-hydroxyphenyl)-1-(2,2,2-trifluoroethyl)-1H-[1,2,4]triazole.

2. The prothrombin time reagent according to claim 1, comprising the at least one iron chelator at a concentration of 0.007 to 2.5 mmol/L.

3. The prothrombin time reagent according to claim 1, further comprising $Ca^{2+}$ ions.

4. The prothrombin time reagent according to claim 3 comprising 5 to 500 mmol/L calcium chloride.

5. The prothrombin time reagent according to claim 1, wherein the tissue factor protein is selected from the group consisting of human or animal recombinant tissue factor protein and natural human or animal tissue factor protein from a tissue extract.

6. A method for preparing a liquid prothrombin time reagent comprising tissue factor protein and phospholipids, the method comprising filling a reagent vial with a liquid comprising tissue factor protein, phospholipids and at least one iron chelator without lyophilization, wherein the at least one iron chelator is a 3,5-diphenyl-1,2,4-triazole selected from the group consisting of deferasirox, ethyl [3,5-bis(2-hydroxyphenyl)-[1,2,4]triazol-1-yl]acetate, and 3,5-bis(2-hydroxyphenyl)-1-(2,2,2-trifluoroethyl)-1H-[1,2,4]triazole.

7. A method for stabilizing a prothrombin time reagent comprising tissue factor protein and phospholipids, the method comprising adding at least one iron chelator the reagent, wherein the at least one iron chelator is a 3,5-diphenyl-1,2,4-triazole selected from the group consisting of deferasirox, ethyl [3,5-bis(2-hydroxyphenyl)-[1,2,4]triazol-1-yl]acetate, and 3,5-bis(2-hydroxyphenyl)-1-(2,2,2-trifluoroethyl)-1H-[1,2,4]triazole.

8. The method according to claim 7, wherein the at least one iron chelator is added in an amount such that the reagent comprises the at least one iron chelator at a concentration of 0.007 to 2.5 mmol/L.

9. A method for determining a coagulation parameter in a plasma sample, the method comprising mixing the plasma sample with the prothrombin time reagent according to claim 1 to give a reaction mixture and determining the coagulation parameter in the reaction mixture.

10. The method according to claim 9, wherein the coagulation parameter is prothrombin time, derived fibrinogen, or endogenous thrombin potential.

11. The method according to claim 9, wherein a change in absorption of the reaction mixture is measured photometrically and a time from the time point of mixing of the prothrombin time reagent with the plasma sample until reaching a threshold value is determined.

12. The method according to claim 7, wherein the at least one iron chelator is added in an amount such that the reagent comprises the at least one iron chelator at a concentration of 0.01 to 0.5 mmol/L.

13. The prothrombin time reagent according to claim 1, comprising the at least one iron chelator at a concentration of 0.01 to 0.5 mmol/L.

14. The prothrombin time reagent of claim 1, wherein the prothrombin time reagent is a liquid.

15. The method of claim 6, wherein the liquid prothrombin time reagent comprises $Ca^{2+}$ ions.

16. The method of claim 7, wherein the prothrombin time reagent comprises $Ca^{2+}$ ions.

\* \* \* \* \*